United States Patent [19]

Mihm et al.

[11] Patent Number: 5,002,943
[45] Date of Patent: Mar. 26, 1991

[54] CONDENSED DIAZEPINONES, PROCESSES FOR PREPARING THEM AND PHARMACEUTICAL COMPOSITIONS CONTAINING THESE COMPOUNDS

[76] Inventors: Gerhard Mihm, Nickeleshalde 5/1; Wolfgang Eberlein, Obere Au 6; Wolfhard Engel, Mozartstrasse 13, all of D-7950 Biberach 1; Gunter Trummlitz, Buchenweg 27, D-7951 Biberach 1; Norbert Mayer, Friedrich-Ebert-Strasse 66, D-7950 Biberach, all of Fed. Rep. of Germany; Adrian de Jonge, De Boomgard 19, NL-3971 LD Driebergen, Netherlands; Henri Doods, Hornsteinweg 7, D-7951 Wathausen, Fed. Rep. of Germany

[21] Appl. No.: 366,828

[22] Filed: Jun. 15, 1989

[30] Foreign Application Priority Data

Jun. 15, 1988 [DE] Fed. Rep. of Germany ....... 3820346

[51] Int. Cl.$^5$ .................... A61K 31/55; C07D 471/04
[52] U.S. Cl. .................................. 514/220; 548/495
[58] Field of Search .................. 540/495; 514/220

[56] References Cited

U.S. PATENT DOCUMENTS

| 4,210,648 | 7/1980 | Schmidt | 514/220 |
| 4,311,700 | 1/1982 | Schaefer | 540/495 |
| 4,931,436 | 6/1990 | Ensel | 514/220 |

FOREIGN PATENT DOCUMENTS

| 0039519 | 11/1981 | European Pat. Off. |
| 0057428 | 8/1982 | European Pat. Off. |
| 0213293 | 3/1987 | European Pat. Off. |
| 0254955 | 2/1988 | European Pat. Off. |
| 0273239 | 7/1988 | European Pat. Off. |

Primary Examiner—Robert Gerstl

[57] ABSTRACT

Novel condensed diazepinones of general formula I

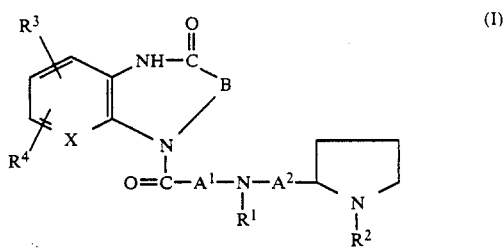

wherein B represents one of the divalent groups

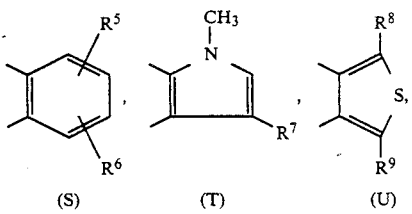

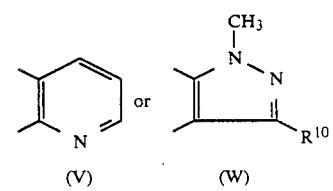

and X, $A^1$, $A^2$ and $R^1$–$R^{10}$ are as defined herein. The condensed diazepinones are suitable as vagal pacemakers for the treatment of bradycardia and bradyarrhythmia and they have spasmolytic effects on peripheral organs, particularly the colon, bladder and bronchi.

4 Claims, No Drawings

CONDENSED DIAZEPINONES, PROCESSES FOR PREPARING THEM AND PHARMACEUTICAL COMPOSITIONS CONTAINING THESE COMPOUNDS

The invention relates to new condensed diazepinones, processes for preparing them and pharmaceutical compositions containing these compounds.

Condensed diazepinones with anti-ulcerative properties and an inhibitory effect on the secretion of gastric juices have already been described in published European applications 0 039 519 and 0 057 428 and from U.S. Pat. Nos. 3,660,380; 3,691,159; 4,213,984; 4,213,985; 4,210,648; 4,410,527; 4,424,225; 4,424,222 and 4,424,226.

It is also known from published European application 0 156 191 that valuable pharmacological properties completely different from those of the compounds of the publications mentioned above can be induced by the introduction of new aminoacyl groups. Compared with these compounds, the condensed diazepinones according to the invention are distinguished by substantially greater activity and resorption after oral administration, whilst having comparable or better selectivity.

The new condensed diazepinones have the general formula

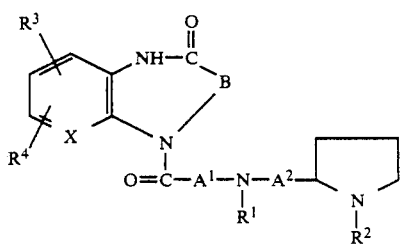

wherein B represents one of the divalent groups

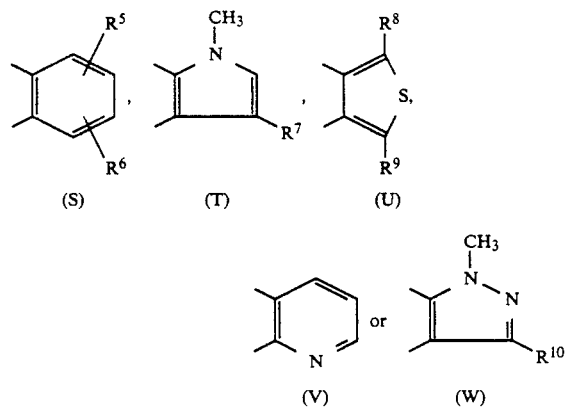

and

X, $A^1$, $A^2$ and $R^1$ to $R^{10}$ are defined as follows:

X represents a $=CH$ group or a nitrogen atom;

$A^1$ and $A^2$ are straight-chained saturated alkylene groups having 1 to 4 carbon atoms;

$R^1$ and $R^2$ are hydrogen atoms or branched or unbranched alkyl groups having 1 to 4 carbon atoms or cycloalkyl groups having 4 to 7 carbon atoms, which may optionally also be substituted by a hydroxy group;

$R^5$ and $R^6$ is an alkyl group having 1 to 4 carbon atoms, or a chlorine or hydrogen atom;

$R^4$ is a hydrogen atom or a methyl group;

$R^5$ and $R^6$ each are hydrogen, fluorine, chlorine, bromine, or an alkyl group having 1 to 4 carbon atoms, with the proviso that if X is nitrogen, $A^2$ is a straight-chained saturated alkylene group having 2 to 4 carbon atoms and $R^1$ is hydrogen, then $R^5$ and $R^6$ cannot both be hydrogen;

$R^7$ represents a hydrogen or chlorine atom or a methyl group;

$R^8$ represents a hydrogen atom or an alkyl group having 1 to 4 carbon atoms;

$R^9$ represents a hydrogen or halogen atom or an alkyl group having 1 to 4 carbon atoms and $R^{10}$ represents a hydrogen atom or a methyl group.

If B represents the divalent group (T) and $R^7$ is a hydrogen atom, $R^3$ cannot represent a chlorine atom; if B represents the divalent group (V), X cannot represent a nitrogen atom.

The compounds of general formula I may also occur in the form of the physiologically acceptable salts thereof after reaction with inorganic or organic acids. Examples of suitable acids include hydrochloric, hydrobromic, sulphuric, methylsulphuric, phosphoric, tartaric, fumaric, citric, maleic, succinic, gluconic, malic, p-toluenesulphonic, methanesulphonic and amidosulphonic acid.

To illustrate the object of the invention, the following preferred compounds may be mentioned by way of example:

5,11-dihydro-11-[[[2-(1-methyl-2-pyrrolidinyl)ethyl]methylamino]acetyl]-6H-pyrido[2,3-b][1,4]benzodiazepin-6-one, 9-chloro-5,11-dihydro-11-[[[2-(1-methyl-2-pyrrolidinyl)ethyl]ethylamino]acetyl]-6H-pyrido[2,3-b][1,4]benzodiazepin-6-one and 5,10-dihydro-5-[[[2-(1-methyl-2-pyrrolidinyl)ethyl]methylamino]acetyl]-11H-dibenzo[b,e][1,4]diazepin-11-one and the physiologically acceptable salts thereof with inorganic or organic acids.

According to the invention, the new base-substituted condensed diazepinones of general formula I are obtained by the following processes:

(a) Base-substituted condensed diazepinones of general formula Ia

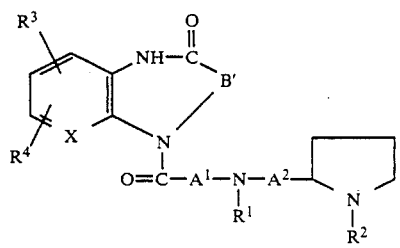

wherein X, $A^1$, $A^2$ and $R^1$ to $R^4$ are defined as hereinbefore and B' represents one of the divalent groups (S), (U), (V), (W) or (T')

wherein $R^{7'}$ is a chlorine atom or a methyl group, are obtained by reacting haloacyl compounds of general formula II

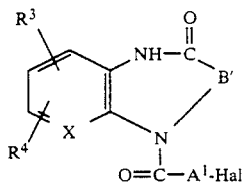
(II)

wherein X, $A^1$, $R^3$, $R^4$ and B= are defined as hereinbefore and Hal represents a chlorine, bromine or iodine atom, with amines of general formula III

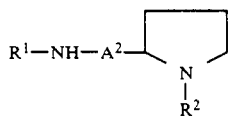
(III)

wherein $R^1$, $R^2$ and $A^2$ are defined as hereinbefore.

Amination is carried out in an inert solvent at temperatures of between $-10°$ C. and the boiling temperature of the solvent, preferably either with at least 2 moles of secondary amine of general formula III or with 1 to 2 moles of a secondary amine of general formula III and an auxiliary base. Examples of solvents include chlorinated hydrocarbons such as methylene chloride, chloroform or dichloroethane; open-chained or cyclic ethers such as diethyl ether, tetrahydrofuran or dioxan; aromatic hydrocarbons such as benzene, toluene, xylene, chlorobenzene or pyridine; alcohols such as ethanol or isopropanol; ketones such as acetone; acetonitrile, dimethylformamide or 1,3-dimethyl-2-imidazolidinone. Examples of auxiliary bases include tertiary organic bases such as triethylamine, N-methylpiperidine, diethylaniline, pyridine and 4-(dimethylamino)pyridine or inorganic bases such as alkali metal or alkaline earth metal carbonates or hydrogen carbonates, hydroxides or oxides. If necessary, the reaction may be accelerated by the addition of alkali metal iodides. The reaction times will range from 15 minutes to 80 hours, depending on the nature and quantity of the amine of general formula III used.

(b) The same base-substituted condensed diazepinones of general formula Ia are also obtained by acylating diazepinones of general formula IV

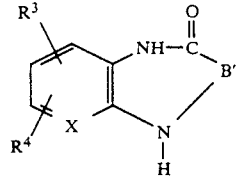
(IV)

wherein X, $R^3$, $R^4$ and B' are defined as hereinbefore, with carboxylic acid derivatives of general formula V

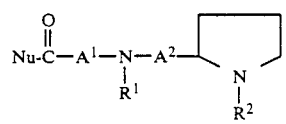
(V)

wherein $A^1$, $A^2$, $R^1$ and $R^2$ are defined as hereinbefore and Nu represents a nucleofugic group or leaving group.

The reaction of the compounds of general formula IV with the acid derivatives of general formula V is carried out in a manner known per se. The leaving group Nu is a group which forms a reactive carboxylic acid derivative together with the carbonyl group to which it is bound. Examples of reactive carboxylic acid derivatives include acid halides, esters, anhydrides or mixed anhydrides, such as those formed from salts of the corresponding acids (Nu=OH) and acid chlorides such as phosphorus oxychloride, diphosphoric acid tetrachloride or chloroformic acid esters or the N-alkyl-2-acyloxypyridinium salts formed when compounds of general formula V (Nu=OH) are reacted with N-alkyl-2-halopyridinium salts.

Preferably, the reaction is carried out with the mixed anhydrides of strong mineral acids, particularly dichlorophosphoric acid. The reaction is optionally effected in the presence of an acid binding agent (proton acceptor). Examples of suitable proton acceptors include alkali metal carbonates or hydrogen carbonates such as sodium carbonate or potassium hydrogen carbonate; tertiary organic amines such as pyridine, triethylamine, ethyl diisopropylamine, 4-dimethylaminopyridine, or sodium hydride. The reaction is carried out at temperatures of between $-25$ C. and 130 C. in an inert solvent. Examples of inert solvents include chlorinated aliphatic hydrocarbons such as methylene chloride, 1,2-dichloroethane; open-chained or cyclic ethers such as diethyl ether, tetrahydrofuran or 1,4-dioxan; aromatic hydrocarbons such as benzene, toluene, xylene or o-dichlorobenzene; polar aprotic solvents such as acetonitrile, dimethylformamide or hexamethylphosphoric acid triamide; or mixtures thereof. The reaction times range from 15 minutes to 80 hours depending on the nature and quantity of the acylating agent of general formula V used. It is not necessary to produce the compounds of general formula V in pure form; instead, they can be prepared in situ in the reaction mixture, in known manner.

(c) The new pyrrolo-condensed diazepinones of general formula Ib covered by general formula I,

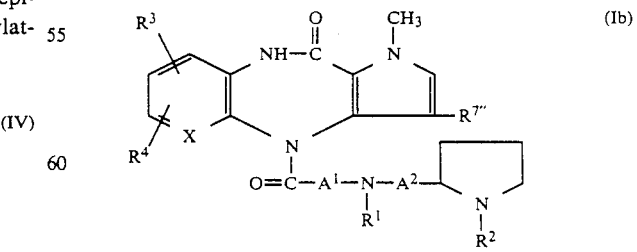
(Ib)

wherein X, $A^1$, $A^2$ and $R^1$ to $R^4$ are defined as hereinbefore and $R7''$ represents a hydrogen atom, may be prepared by hydrogenolysis from compounds of general formula Ib wherein $R7''$ represents a chlorine atom.

The hydrogenolysis is carried out in the presence of catalysts of metals of the VIIIth sub-group of the periodic table of elements, for example palladium on animal charcoal, palladium on barium sulphate, Raney nickel or Raney cobalt, and under hydrogen pressures of from 1 to 300 bar, and at temperatures of from 0° C. to 130° C., in the presence of solvents, for example alcohols such as methanol or ethanol; ethers such as dioxan, tetrahydrofuran; carboxylic acids, e.g. acetic acid; or tertiary amines, for example triethylamine. If the operation is carried out in the absence of additional hydrogen chloride acceptors, for example sodium carbonate, potassium hydrogen carbonate, triethylamine or sodium acetate, the hydrochlorides of the desired compounds are formed directly and may be isolated after removal of the catalyst by evaporation of the reaction solution. If in the above hydrogenolysis reaction the hydrogen is replaced by formic acid, the reaction will in principle be successful even under pressureless conditions. In this alternative embodiment, reaction with formic acid in the presence of dimethylformamide as solvent and palladium on charcoal as catalyst at temperatures of between 70 and 110° C., and reduction with triethylammonium formate in the presence of excess triethylamine, and palladium on animal charcoal or palladium acetate and triarylphosphines such as triphenylphosphine, tris-(o-tolyl)-phosphine, tris-(2,5-diisopropylphenyl)-phosphine, at temperatures of between 40 and 110° C., have proved particularly successful.

Bases of general formula I thus obtained may subsequently be converted into their acid addition salts, or acid addition salts obtained may be converted into the free bases or other pharmacologically acceptable acid addition salts.

The base-substituted condensed diazepinones of general formula I according to the invention contain up to two independent chiral elements, particularly if B represents the divalent group (U). In addition to the asymmetric carbon atom in the side chain, the acylated tricyclic group itself, which may occur in two mirror-image forms, must be regarded as a further chiral element. It depends on the nature of the tricyclic group whether the energy barrier for inversion at this centre is so high that the individual isomers are stable at ambient temperature and capable of isolation. It has been found that in compounds of general formula I wherein X is a nitrogen atom and the positions adjacent the diazepinone ring are unsubstituted, the activating energy required is reduced so much that at ambient temperature diastereoisomers can no longer be detected, let alone preparatively separated.

The aminoacylated condensed diazepinones of general formula I according to the invention thus contain up to two chiral centres, one of which is not always configurationally stable at ambient temperature. These compounds may therefore occur in several diastereoisomeric forms or as enantiomeric (+) and (−) forms. The invention includes the individual isomers as well as the mixtures thereof. The diastereomers may be separated on the basis of their different physico-chemical properties, e.g. by fractional recrystallisation from suitable solvents, by high pressure liquid chromatography, column chromatography or gas chromatography.

The separation of any racemates of the compounds of general formula I may be carried out by known methods, for example using an optically active acid such as (+)− or (−)− tartaric acid or a derivative thereof such as (+)− or (−)− diacetyltartaric acid, (+)− or (−)− monomethyltartrate or (+)− camphorsulphonic acid.

According to a conventional method of separating isomers, the racemate of a compound of general formula I is reacted with one of the optically active acids specified above in equimolar quantities in a solvent and the crystalline diastereoisomeric salts obtained are separated, using their different solubilities. This reaction may be carried out in any type of solvent provided that the latter exhibits sufficiently different solubilities for the salts. Preferably, methanol, ethanol or mixtures thereof, e.g. in a ratio by volume of 50:50, are used. Each of the optically active salts is then dissolved in water, neutralised with a base such as sodium carbonate or potassium carbonate and in this way the corresponding free compound is obtained in the (+) or (−) form.

A single enantiomer or a mixture of two optically active diastereoisomeric compounds covered by general formula I may also be obtained by carrying out the syntheses described above with only one enantiomer of general formula III or V.

The haloacyl compounds of general formula II are prepared by known methods (cf. U.S. Pat. No. 4,550,107).

Intermediate compounds of general formula III can easily be synthesised using methods known to those skilled in the art, e.g. by reduction of corresponding pyrrolidine carboxylic acid alkylamides with lithium aluminium hydride or diborane.

The starting compounds of general formula V wherein Nu represents an alkoxy group are obtained by reacting diamines of general formula III with halocarboxylic acid esters, optionally using additional auxiliary bases, e.g. triethylamine, or catalysts such as Triton B. By saponification of the resulting esters, e.g. with barium hydroxide solution, the carboxylic acids covered by general formula V are obtained, which may be used to prepare derivatives with other nucleofugic groups.

The invention further relates to pharmaceutical compositions which contain one or more condensed diazepinones of general formula I or the physiologically acceptable salts thereof.

For this purpose, the compounds of general formula I can be incorporated in known manner into conventional pharmaceutical preparations such as solutions, suppositories, plain or coated tablets, capsules or infusions. The daily dosage is generally between 0.02 and 5 mg/kg, preferably between 0.02 and 2.5 mg/kg, more particularly between 0.05 and 1.0 mg/kg of body weight, optionally administered in the form of several, preferably 1 to 3, individual doses, in order to achieve the desired results.

The base-substituted condensed diazepinones of general formula I and the acid addition salts thereof have valuable properties; in particular, they have favourable effects on heart rate and, in view of their lack of mydriatic effects or inhibitory effects on the secretion of gastric acid or salivation, they are suitable for use as vagal pacemakers in the treatment of bradycardia and bradyarrhythmia in human as well as veterinary medicine; some of the compounds also exhibit spasmolytic properties on peripheral organs, particularly the colon, bladder and bronchi.

A favourable correlation between tachycardiac effects on the one hand and the undesirable effects on pupil size and the secretion of tears, saliva and gastric acid on the other hand, which occur with therapeutic agents having an anticholinergic component, is of particular importance in the therapeutic use of the substances. The following tests show that the compounds according to the invention exhibit surprisingly favourable correlations in this respect.

A. Studies of binding to muscarinic receptors:
In vitro measurement of the $IC_{50}$ value The organs were donated by male Sprague-Dawley rats weighing 180-220 g. After the heart and submandibular gland and cerebral cortex had been removed, all other steps were carried out in ice cold Hepes HCl buffer (pH 7.4; 100 millimolar NaCl, 10 millimolar $MgCl_2$). The whole heart was cut up with scissors. All the organs were then homogenised in a Potter apparatus.

For the binding test the homogenised organs were diluted as follows:
Whole heart 1:400
Cerebral cortex 1:300
Submandibular gland 1:400

The homogenised organs were incubated at a certain concentration of the radioligand and at a series of concentrations of the non-radioactive test substances in an Eppendorf centrifuge tube at 30 C. Incubation lasted 45 minutes. The radioligand used was 0.3 nanomolar $3H$-N-methylscopolamine ($^3H$-NMS). Incubation was ended by the addition of ice cold buffer followed by vacuum filtration. The filters were rinsed with cold buffer and their radioactivity was determined. It represents the sum of specific and non-specific binding of $^3H$-NMS. The proportion of non-specific binding was defined as the radioactivity which was bound in the presence of 1 micromolar quinuclidinylbenzylate. Each measurement was taken four times. The $IC_{50}$ values of the non-labelled test substances were determined graphically. They represent that concentration of test substance at which the specific binding of 3H-NMS to the muscarinic receptors in the various organs was inhibited by 50%. The results can be seen from Table I.

B. Investigation of functional selectivity of the antimuscarinic effect

Substances with antimuscarinic properties inhibit the effects of agonists supplied exogenically or of acetylcholine, which is released from cholinergic nerve endings. The following is a description of some methods that are suitable for the detection of cardioselective antimuscarinic agents.

"In vivo" methods

The objective of the methods was to confirm the selectivity of the antimuscarinic effect. Those substances which had been selected on the basis of "in vitro" tests were tested for their 1. $M_1/M_2$ selectivity in the rat,
2. Salivation-inhibiting effect on the rat and
3. Inhibition of the acetylcholine effect on the bladder, bronchi and heart rate in the guinea pig. 1. $M_1/M_2$ SELECTIVITY IN THE RAT The method used was described by Hammer and Giachetti (Life Sciences 31, 2991-2998 (1982)). 5 minutes after the intravenous injection of increasing doses of the substance, either the right vagus was electrically stimulated (frequency: 25 Hz; pulse width: 2ms; duration of stimulus: 30s; voltage: supramaximal) or 0.3 mg/kg of McN-A-343 were intravenously injected into male THOM rats. The bradycardia caused by vagus stimulation and the rise in blood pressure caused by McN-A-343 were determined. The dosage of the substances which reduced either the vagal bradycardia (M2) or the rise in blood pressure (M1) by 50% was determined graphically. For the results see Table II.

2. SALIVATION-INHIBITING EFFECT IN THE RAT

Using the method of Lavy and Mulder (Arch. Int. Pharmacodyn. 178, 437-445, (1969)) male THOM rats anaesthetised with 1.2 g/kg of urethane were given increasing doses of the substance by i.v. route. The secretion of saliva was initiated by subcutaneous administration of 2 mg/kg of pilocarpine. The saliva was absorbed with blotting paper and the surface area covered was measured every 5 minutes by planimetry. The dosage of the substance which reduced the volume of saliva by 50% was determined graphically. For the results see Table II.

3. INHIBITION OF THE EFFECT OF ACETYLCHOLINE ON THE BLADDER, BRONCHI AND HEART RATE IN GUINEA PIGS 5 minutes after the administration of the test substance, 10 microgram/kg of acetylcholine were simultaneously injected intravenously and intra-arterially into anaesthetised guinea pigs. The heart rate was recorded directly by extracorporeal derivation of the ECG, the expiration resistance according to Konzett-Ro ler and contraction of the exposed bladder. In order to determine the inhibition of the acetylcholine activity on the organs under investigation, dosage/activity curves were recorded and from them $-\log ED_{50}$ values were determined. For the results see Table III.

The following compounds, by way of example, were investigated according to the procedures set forth above:

A=5,11-dihydro-[[[2-(1-methyl-2-pyrrolidinyl)-ethyl]-methylamino]acetyl]-6H-pyrido[2,3-b][1,4]benzodiazepin-6-one hydrochloride B=9-chloro-5,11-dihydro-11[[[2-(1-methyl-2-pyrrolidinyl)ethyl]ethylamino]acetyl]-6H-pyrido-[2,3-b][1,4]benzodiazepin-6-one C=5,10-dihydro-5-[[[2-(1-methyl-2-pyrrolidinyl)-ethyl]methylamino]acetyl]-11H-dibenzo[b,e][1,4]-diazepin-11-one hydrochloride and as comparison substances D=11-[[2-[(diethylamino)methyl]-1-piperidinyl]acetyl]-5,11-dihydro-6H-pyrido[2,3-b][1,4]benzodiazepin-6-one (see U.S. Pat. No. 4,550,107)

E=5,11-dihydro-11-[(4-methyl-1-piperazinyl)acetyl]-6H-pyrido[2,3-b][1,4]benzodiazepin-6-one (pirenzepine, see U.S. Pat. No. 3,660,380)

and

F=atropine.

TABLE I

| Receptor Binding Tests in vitro: Results: Receptor Binding Tests $IC_{50}$ [nmol $1^{-1}$] | | | |
|---|---|---|---|
| Substance | Cortex | Heart | Submandibular gland |
| A | 50 | 9 | 80 |
| B | 70 | 10 | 100 |
| C | 8 | 3 | 20 |
| D | 1200 | 140 | 5000 |
| E | 100 | 1500 | 200 |
| F | 2 | 4 | 4 |

The information shown in Table I above shows that the new compounds of general formula I distinguish between muscarinic receptors in different tissues. This is clear from the substantially lower $IC_{50}$ values when the test substances are investigated on preparations from the heart compared with those from the cerebral cortex and submandibular gland.

TABLE II

M₁/M₂ selectivity and salivation-inhibiting activity on the rat:
Results:
−log ED₅₀ [mol kg⁻¹]

| Substance | Heart | Blood pressure | Salivation |
|---|---|---|---|
| A | 7.91 | 7.06 | 6.8 |
| D | 6.42 | 5.63 | 5.00 |
| E | 5.60 | 6.94 | 6.22 |
| F | 7.94 | 7.34 | 7.60 |

TABLE III

Inhibition of acetylcholine activity on the bladder, bronchi and heart rate in the guinea pig:
Results:
−log ED₅₀ [mol kg⁻¹]

| Substance | Heart | Bronchi | Bladder |
|---|---|---|---|
| A | 7.7 | 7.6 | 6.85 |
| B | 7.0 | 6.72 | 6.08 |
| C | 7.54 | 7.53 | 6.63 |
| D | 5.84 | 5.58 | 4.73 |
| E | 5.85 | 6.57 | 5.36 |
| F | 7.70 | 7.96 | 7.03 |

The pharmacological data in Tables II and III above show—in total agreement with the receptor binding studies—that the heart rate is increased by the above-mentioned compounds even at dosages at which there is no restriction in the secretion of saliva.

Moreover, the pharmacological data in Table III above indicate a surprisingly high power of distinction between the heart and smooth muscle.

The above-mentioned substances show a substantially improved effectiveness compared with the known compound D. At the same time, their therapeutically useful selectivity is retained. This results in a reduction in the quantity of drug to be administered to the patient without increasing the risk of muscarinic side effects.

Furthermore, the compounds prepared according to the invention are well tolerated; even in the highest doses administered, no toxic side effects were observed in the pharmacological trials.

The Examples which follow are intended to illustrate the invention:

"Mp." indicates "melting point", "D." indicates "decomposition". Satisfactory elemental analyses, IR, UV and ¹H-NMR spectra are available for all the compounds and mass spectra are available for many of them.

EXAMPLE 1

5,11-Dihydro-8-methyl-11[[[2-(1-methyl-2-pyrrolidinyl)ethyl]amino]acetyl]-6H-pyrido[2,3-b][1,4]benzodiazepin-6-one 9.0 g (0.03 mol) of 11-(chloroacetyl)-5,11-dihydro-8-methyl-6H-pyrido[2,3][1,4]benzodiazepin-6-one, 3.2 g of sodium carbonate and 5.1 g (0.04 mol) of 2-(2-aminoethyl)-1-methylpyrrolidine were refluxed for 2 hours in 120 ml of absolute dioxan. The mixture was filtered while hot, the solvent was evaporated off and the residue was purified by column chromatography on silica gel (eluant: methylene chloride/methanol/cyclo-hexane/ammonia 68/15/15/2 by volume). The eluate was recrystallised from ethyl acetate.

Yield: 1.9 g (16% of theory)
Mp.: 107°–109° C. (ethyl acetate).

EXAMPLE 2

9-Chloro-5,11-dihydro-11-[[[2-(1-methyl-2-pyrrolidinyl)ethyl]amino]acetyl]-6H-pyrido[2,3-b][1,4]benzodiazepin-6-one Prepared analogously to Example 1 from 9-chloro-11-(chloroacetyl)-5,11-dihydro-6H-pyrido[2,3-b][1,4]benzodiazepin-6-one and 2-(2-aminoethyl)-1-methylpyrrolidine in a yield of 17% of theory.

Mp.: 130°–132° C. (ethyl acetate).

EXAMPLE 3

6,11-Dihydro-11-[[[2-(1-methyl-2pyrrolidinyl)ethyl]amino]acetyl]-5H-pyrido[2,3-b][1,5benzodiazepin-5-one-dihydrochloride Prepared analogously to Example 1 from 11-(chloroacetyl)6,11-dihydro-5H-pyrido[2,3-b][1,4]benzodiazepin-5-one and 2-(2-aminoethyl)-1-methyl-pyrrolidine. The base was converted into the dihydrochloride by the addition of aqueous hydrochloric acid.

Yield: 14% of theory.
Mp.: 206°–207° C. (isopropanol).

EXAMPLE 4

5,10-Dihydro-5[[[2-(1-methyl-2-pyrrolidinyl)ethyl]amino]acetyl]-11H-dibenzo[b,e][1,4]diazepin-11-one dihydrochloride Prepared analogously to Example 1 from 5-(chloroacetyl)-5,10-dihydro-11H-dibenzo[b,e][1,4-]diazepin-11-one and 2-(2-aminoethyl)-1-methylpyrrolidine. The base was converted into the dihydrochloride by the addition of aqueous hydrochloric acid.

Yield: 13% of theory.
Mp.: 215°–217° C. (isopropanol).

EXAMPLE 5

4,9-Dihydro-4-[[[2-(1-methyl-2-pyrrolidinyl)ethyl]amino]acetyl]-10H-thieno[3,4-b][1,5]benzodiazepin-10-one dihydrochloride Prepared analogously to Example 1 from 4-(chloroacetyl)-4,9-dihydro-10H-thieno[3,4-b][1,5]benzodiazepin-10-one and 2-(2-aminoethyl)-1-methylpyrrolidine. The base was converted into the dihydrochloride by the addition of aqueous hydrochloric acid.

Yield: 20% of theory.
Mp.: 223°–225° C. (isopropanol).

EXAMPLE 6

1,3-Dimethyl-4-[[[2-(1-methyl-2-pyrrolidinyl)ethyl]amino]acetyl]-1,4,9,10-tetrahydropyrazolo-[4,3-e]pyrido[3,2-b]diazepin-10-one difumarate Prepared analogously to Example 1 from 4-(chloroacetyl)-1,3-dimethyl-1,4,9,10-tetrahydro-pyrazolo[4,3-e]pyrido[3,2-b]diazepin-10-one and 2-(2-(aminoethyl)-1-methylpyrrolidine. The base was converted into the fumarate with fumaric acid.

Yield: 30% of theory.
Mp.: 200°–202° C. (isopropanol).

EXAMPLE 7

5,11-Dihydro-11-[[[2-(1-ethyl-2-pyrrolidinyl)ethyl]amino]acetyl]-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 2-(2-aminoethyl)-1-ethylpyrrolidine.
Yield: 9.5% of theory,
Mp.: 109°–111° C. (ethyl acetate/cyclohexane 2/1 v/v).

EXAMPLE 8

5,11-Dihydro-11-[3-[[2-(1-methyl-2-pyrrolidinyl)ethyl]amino]propionyl]-6H-pyrido[2,3-b][1,4]benzodiazepin-6-one 3.85 g (0.03 mol) of 2-(2-aminoethyl)-1-methyl-pyrrolidine were added dropwise to a solution of 7.1 g (0.024 mol) of 11-(3-chloropropionyl)-5,11-dihydro-6H-pyrido[2,3-b][1,4]benzodiazepin-6-one and 3 g of triethylamine in 70 ml of dimethylformamide at ambient temperature and the resulting mixture was stirred at this temperature for a further 2 hours. After the solvent had been evaporated off, the residue was purified by column chromatography on silica gel (mobile phase: ethylene chloride/methanol/ammonia 100/20/2 by volume). The amorphous solid substance obtained was not crystalline.
Yield: 2.93 g (31% of theory)
$R_F$=0.23 (Merck ready-made plates, silica gel F 254; eluant: ethyl acetate/methanol/conc. ammonia 70/30/5 by volume).

EXAMPLE 9

5,10-Dihydro-5-[3-[[2-(1-methyl-2-pyrrolidinyl)ethyl]amino]propionyl]-11H-dibenzo[b,e][1,4]benzodiazepin-11-one Prepared analogously to Example 8 from 5-(3-chloropropionyl)-5,10-dihydro-11H-dibenzo[b,e][1,4]diazepin-11-one and 2-(2-amino-ethyl)-1-methylpyrrolidine as an amorphous solid.
Yield: 13% of theory.
$R_F$=0.34 (Merck ready-made plates, silica gel F 254; eluant: ethyl acetate/methanol/conc. ammonia 70/30/5 by volume).

EXAMPLE 10

5,11-Dihydro-11-[[[2-(1-methyl-2-pyrrolidinyl)ethyl]methylamino]acetyl]-6H-pyrido[2,3-b][1,4benzodiazepin-6-one hydrochloride A solution of 28.7 g (0.1 mol) of 11-(chloroacetyl)-5,11-dihydro-6H-pyrido[2,3-b][1,4]benzodiazepin-6-one and 15.7 g (0.11 mol) of 1-methyl-2-[2-(methylamino)ethyl]pyrrolidine in 300 ml of absolute dimethylformamide was stirred for 8 hours at ambient temperature. After the solvent had been distilled off the residue was triturated with a little methanol. The crystals precipitated were suction-filtered and purified by recrystallisation from ethyl acetate/methanol using activated charcoal.
Yield: 19.8 g (46% of theory)
Mp.: 223°–224° C. (ethyl acetate/methanol).

EXAMPLE 11

5,10-Dihydro-5-[[[2-(1-methyl-2-pyrrolidinyl)ethy]methylamino]acetyl]-11H-dibenzo[b,e][1,4]diazepin-11-one hydrochloride Prepared analogously to Example 10 from 5-(chloroacetyl)-5,10-dihydro-11H-dibenzo[b,e][1,4]-diazepin-11-one and 1-methyl-2-[2-(methylamino)ethyl]-pyrrolidine.
Yield: 42% of theory.
Mp.: 208°–210° C. (ethyl acetate/methanol).

EXAMPLE 12

5,11-Dihydro-11-[[[2-(1-methyl-2-pyrrolidinyl)ethyl]ethylamino]acetyl]6H-pyrido[2,3-b][1,4]benzodiazepin-6-one 3.1 g (0.022 mol) of 1-methyl-2-[2-(ethylamino)ethyl]-pyrrolidine were added dropwise to a solution of 5.7 g (0.02 mol) of 11-(chloroacetyl)-5,11-dihydro-6H-pyrido[2,3-b][1,4]benzodiazepin-6-one and 2.8 ml of triethylamine in 50 ml of dimethylformamide and the mixture was stirred for a further 0.5 hours at ambient temperature. After the solvent had been distilled off, the residue was chromatographed on silica gel (mobile phase: methylene chloride/methanol 9/1 v/v). The concentrated eluates were distributed between potassium carbonate solution and ethyl acetate. After the solvent had been distilled off, the crystals obtained were recrystallised from diisopropylether/ethyl acetate.
Yield: 0.98 g (12% of theory)
Mp.: 159°–160° C. (diisopropyl ether/ethyl acetate).

EXAMPLE 13

9-Chloro-5,11-dihydro-11-[[[2-(1-methyl-2-pyrrolidinyl)ethyl]ethylamino]acetyl]-6H-pyrido[2,3-b][1,4]benzodiazepin-6-one A solution of 3.2 g (0.01 mol) of 9-chloro-11-(chloroacetyl)-5,11-dihydro-6H-pyrido[2,3-b][1,4]benzodiazepin-6-one, 1.6 g (0.01 mol) of methyl-2-[2-(ethylamino)ethyl]pyrrolidine and 3 g of potassium carbonate in 100 ml of acetonitrile were stirred at 60 C. for 2 hours, the solvent was distilled off in vacuo, the residue was stirred with water and extracted with methylene chloride. The crystals obtained after purification by column chromatography on silica gel (mobile phase: ethyl acetate/methanol/conc. ammonia 70/30/3 v/v/v) and evaporation of the eluates were recrystallised from diisopropyl ether/methanol.
Yield: 0.15 g (3.5% of theory)
Mp.: 164°–165° C. (diisopropyl ether/methanol).

EXAMPLE 14

5,10-Dihydro-5-[[[2-(1-methyl-2-pyrrolidinyl)ethyl]ethylamino]acetyl]-11H-dibenzo[b,e][1,4]diazepin-11-one Prepared analogously to Example 13 from 5-(chloroacetyl)-5,10-dihydro-11H-dibenzo[b,e][1,4]-diazepin-11-one and 1-methyl-2-[2-(ethylamino)ethyl]-pyrrolidine.
Yield: 3.5% of theory.
RF=0.65 (Merck ready-made plates, silica gel F 254; eluant: ethyl acetate/methanol/conc. ammonia 70/30/5 v/v/v).

EXAMPLE 15

6,11-Dihydro-11-[[[2-(1-methyl-2-pyrrolidinyl)ethyl]ethylamino]acetyl]-5H-pyrido[2,3-b][1,5]benzodiazepin-5-one Prepared analogously to Example 13 from 11-(chloro-acetyl)-6,11-dihydro-5H-pyrido[2,3-b][1,5]benzodiazepin-5-one and 1-methyl-2-[2-(ethylamino)ethyl]-pyrrolidine.
Yield: 13% of theory.
Mp.: 139°–140° C. (diisopropyl ether/ethyl acetate/acetone).

The following Examples illustrate the preparation of some pharmaceutical administration forms:

EXAMPLE I

Tablets containing 5 mg 5,11-dihydro-11-[[[2-(1-methyl-2-pyrrolidinyl)ethyl]methylamino]acetyl]-6H-pyrido-[2,3-b][1,4]benzodiazepin-6-one

| Composition: 1 tablet contains: | |
|---|---|
| Active substance | 5.0 mg |
| Lactose | 148.0 mg |
| Potato starch | 65.0 mg |
| Magnesium stearate | 2.0 mg |
| | 220.0 mg |

Method of preparation

A 10% mucilage is prepared from potato starch by heating. The active substance, lactose and remaining potato starch are mixed together and granulated with the above mucilage through a 1.5 mm mesh screen. The granules are dried at 45° C., rubbed through the same screen again, mixed with magnesium stearate and compressed to form tablets.

Weight of tablet: 220 mg
Punch: 9 mm

EXAMPLE II

Coated tablets containing 5 mg of 5,11-dihydro-11-[[[2-(1-methyl-2-pyrrolidinyl)ethyl]methylamino]acetyl]-6H-pyrido[2,3-b][1,4]benzodiazepin-6-one The tablets prepared according to Example I are coated, by a known method, with a coating consisting essentially of sugar and talc. The finished coated tablets are polished with beeswax.

Weight of coated tablet: 300 mg

EXAMPLE III

Ampoules containing 10 mg of 5,11-dihydro-11-[[[2-(1-methyl-2-pyrrolidinyl)ethyl]methylamino]acetyl]-6H-pyrido[2,3-b][1,4]benzodiazepin-6-one

| Composition: 1 ampoule contains: | | |
|---|---|---|
| Active substance | | 10.0 mg |
| Sodium chloride | | 8.0 mg |
| Distilled water | ad | 1 ml |

Method of preparation

The active substance and sodium chloride are dissolved in distilled water and then made up to the volume specified. The solution is sterile filtered and transferred into 1 ml ampoules.

Sterilisation: 20 minutes at 120° C.

EXAMPLE IV

Suppositories containing 20 mg of 5,11-dihydro-11-[[[2-(1-methyl-2-pyrrolidinyl)ethyl]methylamino]acetyl]-6H-pyrido[2,3-b][1,4]benzodiazepin-6-one

| Composition: 1 suppository contains: | |
|---|---|
| Active substance | 20.0 mg |
| Suppository mass (e.g. Witepsol W 45 ®) | 1 680.0 mg |
| | 1 700.0 mg |

Method of operation

The finely powdered active substance is suspended in the molten suppository mass which has been cooled to 40° C. The mass is poured at 37° C. into slightly chilled suppository moulds.

Weight of suppository: 1.7 g.

EXAMPLE V

Drops containing 5,11-dihydro-11-[[[2-(1-methyl-2-pyrrolidinyl)ethyl]methylamino]acetyl]-6H-pyrido-[2,3-b][1,4]benzodiazepin-6-one

| Composition: 100 ml of drops solution contain: | | |
|---|---|---|
| Methyl p-hydroxybenzoate | | 0.035 g |
| Propyl p-hydroxybenzoate | | 0.015 g |
| Aniseed oil | | 0.05 g |
| Menthol | | 0.06 g |
| Pure ethanol | | 10.0 g |
| Active substance | | 0.5 g |
| Sodium cyclamate | | 1.0 g |
| Glycerol | | 15.0 g |
| Distilled water | ad | 100.0 ml |

Method of operation

The active substance and sodium cyclamate are dissolved in about 70 ml of water and glycerol is added. The p-hydroxybenzoates, aniseed oil and menthol are dissolved in ethanol and this solution is added with stirring to the aqueous solution. Finally, the solution is made up to 100 ml with water and filtered to remove any suspended particles.

What is claimed is:

1. A method for treating bradycardia and bradyarrhythmia in a patient, which comprises administering to the patient a therapeutically effective amount of the condensed diazepinone of the formula

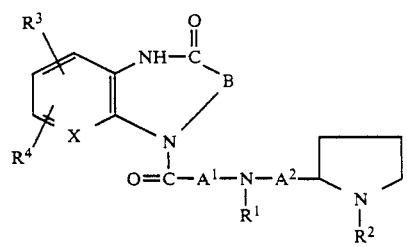

wherein B is one of the divalent groups

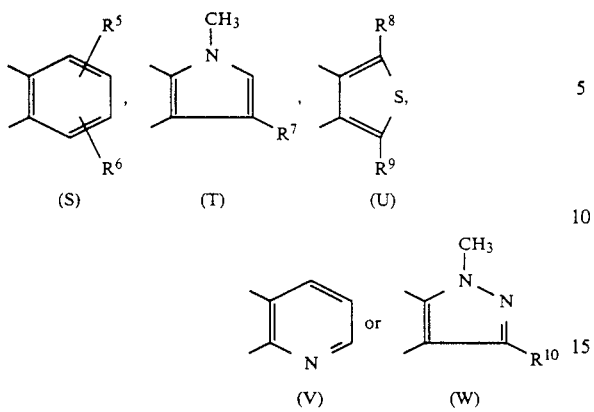

(S)  (T)  (U)

(V)  (W)

X is a =CH— group or nitrogen;

A¹ and A² are each a straight-chained saturated alkylene group having 1 to 4 carbon atoms;

R¹ and R² each are hydrogen, a branched or unbranched alkyl group having 1 to 4 carbon atoms, or a cycloalkyl group having 4 to 7 carbon atoms, which alkyl group or cycloalkyl group is unsubstituted or substituted with a hydroxy group;

R³ is chlorine, hydrogen, or an alkyl group having 1 to 4 carbon atoms;

R⁴ is hydrogen or a methyl group;

R⁵ and R⁶ each are hydrogen, fluorine, chlorine, bromine, or an alkyl group having 1 to 4 carbon atoms, with the proviso that if X is nitrogen, A² is a straight-chained saturated alkylene group having 2 to 4 carbon atoms and R¹ is hydrogen, then R⁵ and R⁶ cannot both be hydrogen;

R⁷ is hydrogen, chlorine, or a methyl group;

R⁸ is hydrogen or an alkyl group having 1 to 4 carbon atoms;

R⁹ is hydrogen, halogen, or an alkyl group having 1 to 4 carbon atoms and

R¹⁰ is hydrogen or a methyl group, wherein if B is the divalent group (T) and R⁷ is hydrogen, R³ cannot be a chlorine; and wherein if B is the divalent group (V), X cannot be nitrogen, the isomers or enantiomers thereof, and the physiologically acceptable acid addition salts thereof with inorganic or organic acids.

2. A method for treating bradycardia and bradyarrthythmia in a patient, as recited in claim 1 wherein the condensed diazepinone is selected from the group consisting of:

5,11-dihydro-11-[[[2-(1-methyl-2-pyrrolidinyl)ethyl]methylamino]acetyl]-6H-pyrido[2,3-b][1,4]benzodiazepin-6-one;

9-chloro-5,11-dihydro-11-[[[2-(1-methyl-2-pyrrolidinyl)ethyl]ethylamino]acetyl]-6H-pyrido[2,3-b][1,4]benzodiazepin-6-one;

5,10-dihydro-5-[[[2-(1-methyl-2-pyrrolidinyl)ethyl]methylamino]acetyl]-11H-dibenzo[b,e][1,4]diazepin-11-one;

and the physiologically acceptable salts thereof with inorganic or organic acids.

3. A method for treating spasm in the colon, bladder or bronchi of a patient which comprises administering to the patient a therapeutically effective amount of the condensed diazepinone of the formula

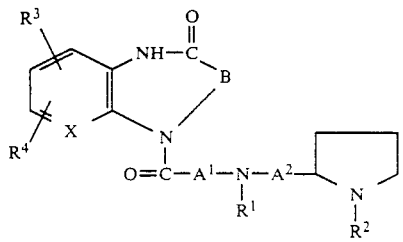

wherein B is one of the divalent groups

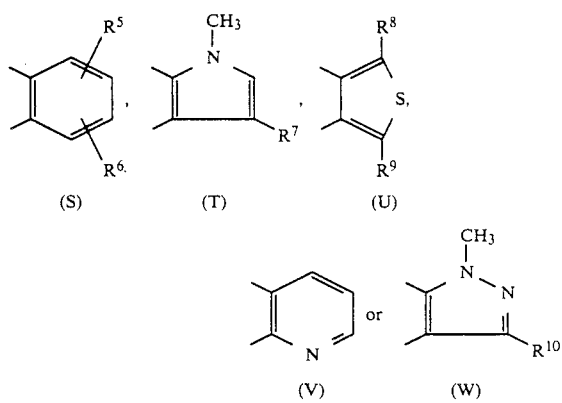

(S)  (T)  (U)

(V)  (W)

X is a =CH— group or nitrogen;

A¹ and A² are each a straight-chained saturated alkylene group having 1 to 4 carbon atoms;

R¹ and R² each are hydrogen, a branched or unbranched alkyl group having 1 to 4 carbon atoms, or a cycloalkyl group having 4 to 7 carbon atoms, which alkyl group or cycloalkyl group is unsubstituted or substituted with a hydroxy group;

R³ is chlorine, hydrogen, or an alkyl group having 1 to 4 carbon atoms;

R⁴ is hydrogen or a methyl group;

R⁵ and R⁶ each are hydrogen, fluorine, chlorine, bromine, or an alkyl group having 1 to 4 carbon atoms, with the proviso that if X is nitrogen, A² is a straight-chained saturated alkylene group having 2 to 4 carbon atoms and R¹ is hydrogen, then R⁵ and R⁶ cannot both be hydrogen;

R⁷ is hydrogen, chlorine, or a methyl group;

R⁸ is hydrogen or an alkyl group having 1 to 4 carbon atoms;

R⁹ is hydrogen, halogen, or an alkyl group having 1 to 4 carbon atoms and

R¹⁰ is hydrogen or a methyl group, wherein fi B is the divalent group (T) and R⁷ is hydrogen, R³ cannot be a chlorine; and wherein if B is the divalent group (V), X cannot be nitrogen, the isomers or enantiomers thereof, or the physiologically acceptable acid addition salts thereof with inorganic or organic acids.

4. A method for treating spasm in the colon, bladder or bronchi for a patient as recited in claim 3 wherein the condensed diazepinone is selected from the group consisting of:

5,11-dihydro-11-[[[2-(1-methyl-2-pyrrolidinyl)ethyl]methylamino]acetyl]-6H-pyrido[2,3-b][1,4]benzodiazepin-6-one;

9-chloro-5,11-dihydro-11-[[[2-(1-methyl-2-pyrrolidinyl)ethyl]ethylamino]acetyl]-6H-pyrido[2,3-b][1,4]benzodiazepin-6-one;

5,10-dihydro-5-[[[2-(1-methyl-2-pyrrolidinyl)ethyl]methylamino]acetyl]-11H-dibenzo[b,e][1,4]diazepin-11-one;

and the physiologically acceptable salts thereof with inorganic or organic acids.

* * * * *